United States Patent
Wang et al.

(10) Patent No.: US 7,425,652 B2
(45) Date of Patent: Sep. 16, 2008

(54) PREPARATION OF ALKANOLAMINES

(75) Inventors: Wei Wang, Boothwyn, PA (US); Farhad Fadakar, Downingtown, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/190,321

(22) Filed: Jul. 27, 2005

(65) Prior Publication Data

US 2007/0027056 A1 Feb. 1, 2007

(51) Int. Cl.
*C07C 7/00* (2006.01)
*C07C 209/00* (2006.01)
*C07C 213/00* (2006.01)
*C07C 239/00* (2006.01)

(52) U.S. Cl. .......................... 564/2; 564/300; 564/497; 510/499; 510/505

(58) Field of Classification Search ........................ None
See application file for complete search history.

(56) References Cited

U.S. PATENT DOCUMENTS

| | | | | |
|---|---|---|---|---|
| 2,901,513 A * | 8/1959 | Thomas | ........................... | 564/2 |
| 3,207,790 A | 9/1965 | Glew et al. | ................... | 260/584 |
| 3,819,710 A | 6/1974 | Jordan | ......................... | 260/584 |
| 5,279,771 A * | 1/1994 | Lee | ............................. | 510/212 |
| 5,331,102 A * | 7/1994 | Gibson | ........................ | 564/498 |
| 5,334,332 A * | 8/1994 | Lee | ............................. | 510/175 |
| 5,847,221 A | 12/1998 | Gibson | ........................ | 564/498 |
| 6,140,287 A * | 10/2000 | Lee | ............................. | 510/175 |
| 6,291,715 B1 | 9/2001 | Ruider et al. | ............... | 564/497 |
| 6,319,885 B1 * | 11/2001 | Lee et al. | ..................... | 510/175 |
| 6,323,371 B2 | 11/2001 | Ruider et al. | ............... | 564/497 |
| 6,388,137 B1 | 5/2002 | Ruider et al. | ............... | 564/499 |
| 6,774,264 B2 | 8/2004 | Delanghe et al. | ............ | 564/497 |

FOREIGN PATENT DOCUMENTS

EP 1132371 A1 9/2001
WO WO01/77050 10/2001

OTHER PUBLICATIONS

C. Longuet et al., "Oligomer Model to Explain the Coloration of TEA and Discoloration Catalytic Treatment," *Journal of Molecular Catalysis A: Chemical* 234 (2005) 59-62.

* cited by examiner

*Primary Examiner*—Gregory R Del Cotto
(74) *Attorney, Agent, or Firm*—Shao-Hua Guo

(57) ABSTRACT

Alkanolamine compositions are disclosed. The composition comprises an alkanolamine and hydroxylamine or hydrazine. Preferred alkanolamine includes diethanolamine, triethanolamine, and mixtures thereof. The composition of the invention has significantly reduced discoloration.

3 Claims, No Drawings

PREPARATION OF ALKANOLAMINES

FIELD OF THE INVENTION

The invention relates to alkanolamines. More particularly, the invention relates to alkanolamines that have improved color stability.

BACKGROUND OF THE INVENTION

Alkanolamines, for example, triethanolamine, are widely used in cosmetic and pharmaceutical products such as soaps, cleaners, and shampoos. One problem associated with the use of alkanolamines is discoloration. That is, during storage, the color of alkanolamines deepens, making them unsatisfactory for certain applications.

Methods for improving color stability of alkanolamines are known. For instance, U.S. Pat. No. 6,323,371 discloses the preparation of alkanolamines having improved color quality by treating the alkanolamines with phosphorous acid or hypophosphorous acid prior to distillation. The pretreatment, although producing alkanolamines having low fresh color, does not effectively prevent the discoloration during the product storage.

U.S. Pat. No. 3,207,790 describes a process for improving the color quality of alkanolamines by the addition of alkali metal borohydride to the alkanolamines. However, the addition of alkali metal borohydride does not produce satisfactory results.

New improvement for the color stability of alkanolamines is needed. Ideally, the alkanolamines would remain on-the-spec color (APHA color less than 50) for at least 3 months at room temperature.

SUMMARY OF THE INVENTION

The invention is an alkanolamine composition. The composition comprises an alkanolamine and a color stabilizer selected from the group consisting of hydroxylamine, hydrazine, and mixtures thereof. Hydroxylamine or hydrazine is present in the composition in an amount effective to reduce the discoloration of the alkanolamine. The composition of the invention remains on-the-spec color (APHA color 50 or less) for at least three months in storage.

DETAILED DESCRIPTION OF THE INVENTION

The composition of the invention comprises an alkanolamine and a color stabilizer selected from the group consisting of hydroxylamine and hydrazine.

The composition of the invention remains on-the-spec color (APHA color 50 or less) for at least three months in storage at a room temperature (below 38° C.). The color is tested according to an empirically developed method. The test is performed at 60° C. Three days of the color stability at 60° C. is equivalent to that of one month at 38° C. Preferably, the composition remains an APHA color less than 50 for 8 weeks at 60° C. (equivalent to about 18 months at 38° C.).

Alkanolamines suitable for the use of the invention include derivatives of ammonia in which one, two, or three hydrogens are replaced by one or more alkanol groups. Preferably, the alkanolamines are ethanolamines or propanolamines. Ethanolamines and propanolamines can be obtained by known processes, e.g., by the reaction of ammonia or a primary or secondary amine with ethylene oxide or propylene oxide. The reaction produces a mixture of monoalkanolamine, dialkanolamine, and trialkanolamine. For instance, the reaction of ammonia with ethylene oxide produces a mixture of monoethanolamine, diethanolamine, and triethanolamine. The mixture is often separated by distillation.

Preferably, the alkanolamine is selected from the group consisting of diethanolamine, triethanolamine, the like, and mixtures thereof. More preferably, the alkanolamine is triethanolamine.

Hydroxylamine or hydrazine is present in the composition in an amount effective to reduce the discoloration of the alkanolamine.

Preferably, hydroxylamine or hydrazine is present in an amount greater than or equal to 10 ppm. More preferably, hydroxylamine or hydrazine is present in the composition in an amount greater than or equal to 50 ppm. Most preferably, hydroxylamine or hydrazine is present in the composition in an amount greater than or equal to 100 ppm. A particularly preferred range of hydroxylamine or hydrazine in the composition is from 100 ppm to 1000 ppm.

The preferred triethanolamine is made by a process that comprises distilling triethanolamine from the mixture of diethanolamine and triethanolamine in the presence of phosphorous acid ($H_3PO_3$). The method of preparation and distillation of triethanolamine is described in, for example, U.S. Pat. No. 6,323,371. The patent teachings are herein incorporated by reference in a jurisdiction where such incorporation is allowed.

Preferably, the composition of the invention further comprises an alkali metal borohydride. Preferred alkali metal borohydride include sodium borohydride ($NaBH_4$) and potassium borohydride ($KBH_4$). Sodium borohydride is more preferred.

The alkali metal borohydride is preferably used in an amount greater than or equal to 10 ppm. The alkali metal borohydride is more preferably used in an amount greater than or equal to 50 ppm. The alkali metal borohydride is most preferably used in an amount greater than or equal to 100 ppm.

We have surprisingly found that using an alkali metal borohydride alone does not satisfactorily reduce discoloration of the alkanolamine. While hydroxylamine or hydrazine alone can effectively reduce the discoloration of the alkanolamine, a combination of hydroxylamine or hydrazine with an alkali metal borohydride produces significantly enhanced results in reducing discoloration of the alkanolamine.

The invention includes a method for reducing discoloration of alkanolamines. The method comprises adding a sufficient amount of hydroxylamine, hydrazine, or a mixture thereof to an alkanolamine. Suitable alkanolamines and suitable amounts of hydroxylamine and hydrazine are the same as discussed above.

Preferably, the method of the invention further comprises adding an alkali metal borohydride to the alkanolamine. Suitable alkali metal borohydrides and their amounts are discussed above.

Preferably, hydroxylamine, hydrazine, alkali metal borohydride are added to pure alkanolamine. The purity of the alkanolamine is preferably greater than 95%, more preferably greater than 99%, and most preferably greater than 99.5%.

The following examples merely illustrate the invention. Those skilled in the art will recognize many variations that are within the spirit of the invention and scope of the claims.

EXAMPLES 1-7 AND COMPARATIVE EXAMPLES C8 AND C9

Triethanolamine (TEA) is fractionally distilled from a mixture of TEA and diethanolamine in the presence of 500 ppm phosphorous acid under vacuum. To freshly-distilled TEA samples are added hydroxylamine (50% aqueous solution), hydrazine (35% aqueous solution), or their mixtures with sodium borohydride, respectively, in Examples 1-7.

In Comparative Example C8, only borohydride, but no hydroxylamine or hydrazine, is added.

In Comparative Example C9, no additive is added.

Color stability of the samples is tested at 60° C. for periods of time specified in Table 1. From Table 1, it can be seen that the compositions containing hydroxylamine or hydrazine have much slower discoloration than pure TEA of Comparative Example C9.

From Table 1, it can also be seen that although sodium borohydride, when used in combination with hydroxylamine or hydrazine, can enhance the color stability, it is much less effective when used alone.

EXAMPLE 10 AND COMPARATIVE EXAMPLES C11 AND C12

TEA is fractionally distilled from a mixture of TEA and diethanolamine in the presence of 1000 ppm phosphorous acid under vacuum. In Example 10, a mixture of hydroxylamine and sodium borohydride is added to a freshly-distilled TEA sample. In Comparative Example C11, only sodium borohydride is added. In Comparative Example C12, no additive is added. From Table 2, it can be seen that the combination of hydrazine and sodium borohydride effectively stabilizes the color of TEA and that sodium borohydride alone is much less effective.

EXAMPLE 13 AND COMPARATIVE EXAMPLES C14 AND C15

TEA is fractionally distilled from a mixture of TEA and diethanolamine in the absence of phosphorous acid under vacuum. In Example 13, a mixture of hydroxylamine and sodium borohydride is added to a freshly-distilled TEA sample. In Comparative Example C14, only sodium borohydride is added. In Comparative Example C15, no additive is added. From Table 3, it can be seen that the combination of hydrazine and sodium borohydride effectively stabilizes the color of TEA and that sodium borohydride alone is much less effective.

Comparing the results in Table 2 with the results in Table 3, it can be seen that distilling TEA in the presence of phosphorous acid can significantly reduce the initial color of TEA. However, it is the addition of hydroxylamine or hydrazine that significantly reduces the discoloration of TEA.

TABLE 1

COLOR STABILITY OF TRIETHANOLAMINE DISTILLED IN THE PRESENCE OF 500 PPM PHOSPHOROUS ACID

| Ex. No. | Additives, ppm | | | APHA Color, days after aged at 60° C. | | | | | | | |
|---|---|---|---|---|---|---|---|---|---|---|---|
| | Hydroxylamine | Hydrazine | Sodium Borohydride | 0 | 3 | 7 | 14 | 21 | 28 | 42 | 56 |
| 1 | 200 | 0 | 0 | 18 | 16 | 23 | 30 | 37 | 39 | 40 | 50 |
| 2 | 400 | 0 | 0 | 18 | 17 | 24 | 30 | 37 | 42 | — | — |
| 3 | 0 | 300 | 0 | 18 | 21 | 28 | 40 | 49 | 55 | — | — |
| 4 | 200 | 0 | 400 | 18 | 9 | 13 | 13 | 18 | 20 | 22 | 26 |
| 5 | 200 | 0 | 200 | 19 | — | 20 | 20 | 25 | 26 | 28 | 30 |
| 6 | 200 | 0 | 100 | 19 | — | 23 | 25 | 26 | 27 | 29 | 30 |
| 7 | 0 | 300 | 400 | 18 | 11 | 15 | 17 | 22 | 23 | — | — |
| C8 | 0 | 0 | 400 | 18 | 21 | 39 | 44 | 61 | — | — | — |
| C9 | 0 | 0 | 0 | 18 | 56 | 102 | — | — | — | — | — |

TABLE 2

COLOR STABILITY OF TRIETHANOLAMINE DISTILLED IN THE PRESENCE OF 1000 PPM PHOSPHOROUS ACID

| Ex. No. | Additives, ppm | | | APHA Color, days after aged at 60° C. | | | | | | | |
|---|---|---|---|---|---|---|---|---|---|---|---|
| | Hydroxylamine | Hydrazine | Sodium Borohydride | 0 | 3 | 7 | 14 | 21 | 28 | 42 | 56 |
| 10 | 200 | 0 | 400 | 21 | 18 | 18 | 18 | 21 | 23 | 26 | 30 |
| C11 | 0 | 0 | 400 | 21 | 46 | 52 | 66 | 70 | 78 | — | — |
| C12 | 0 | 0 | 0 | 21 | 67 | 120 | 145 | 162 | 193 | — | — |

TABLE 3

COLOR STABILITY OF TRIETHANOLAMINE DISTILLED
IN THE ABSENCE OF PHOSPHOROUS ACID

| Ex. No. | Additives, ppm | | | APHA Color, days after aged at 60° C. | | | | | | | |
|---|---|---|---|---|---|---|---|---|---|---|---|
| | Hydroxylamine | Hydrazine | Sodium Borohydride | 0 | 3 | 7 | 14 | 21 | 28 | 42 | 56 |
| 13 | 200 | 0 | 400 | 52 | 47 | 72 | 85 | 98 | 101 | — | — |
| C14 | 0 | 0 | 400 | 52 | 49 | 88 | 166 | 245 | 269 | — | — |
| C15 | 0 | 0 | 0 | 52 | 343 | 426 | 532 | 605 | 659 | — | — |

We claim:

1. A composition consisting of an alkanolamine and a hydroxylamine, wherein hydroxylamine is present in an amount sufficient to stabilize the color of alkanolamine within the range of 100 ppm to 1000 ppm of the composition.

2. The composition of claim 1, wherein the alkanolamine is selected from diethanolamine, triethanolamine, or mixtures thereof.

3. The composition of claim 1, wherein the alkanolamine is triethanolamine.

* * * * *